United States Patent
Zaldívar Larraín

(10) Patent No.: US 10,538,646 B2
(45) Date of Patent: Jan. 21, 2020

(54) MATERIAL COMPRISING A MIXTURE OF BROWN ALGAE, CELLULOSIC MATERIAL AND AN ADHESIVE, AND PRODUCTION METHOD THEREOF

(71) Applicant: Francisco José Zaldívar Larraín, Santiago (CL)

(72) Inventor: Francisco José Zaldívar Larraín, Santiago (CL)

(*) Notice: Subject to any disclaimer, the term of this patent is extended or adjusted under 35 U.S.C. 154(b) by 0 days.

(21) Appl. No.: 15/742,630

(22) PCT Filed: Jun. 3, 2016

(86) PCT No.: PCT/CL2016/050029
§ 371 (c)(1),
(2) Date: Jan. 8, 2018

(87) PCT Pub. No.: WO2017/004731
PCT Pub. Date: Jan. 12, 2017

(65) Prior Publication Data
US 2018/0201764 A1   Jul. 19, 2018

(30) Foreign Application Priority Data
Jul. 7, 2015 (CL) .................................. 1932-2015

(51) Int. Cl.
*C08L 1/02* (2006.01)
*A61K 36/33* (2006.01)
*A61K 36/03* (2006.01)
*C08L 5/00* (2006.01)

(52) U.S. Cl.
CPC ................ *C08L 1/02* (2013.01); *A61K 36/03* (2013.01); *A61K 36/33* (2013.01); *C08L 5/00* (2013.01)

(58) Field of Classification Search
None
See application file for complete search history.

(56) References Cited

U.S. PATENT DOCUMENTS 3,276,359 A * 10/1966 Oransky .................. B41N 1/14
101/460
4,976,821 A * 12/1990 Laapotti .................. D21F 3/04
162/306

(Continued)

FOREIGN PATENT DOCUMENTS

WO    199845221 A1    10/1998
WO    2003046199 A2    6/2003
(Continued)

OTHER PUBLICATIONS

Kelly et al, variations in the alginate content and composition of Durvillaea antarctica and d. willana from southern new zealand, journal of applied phycology, 12, pp. 317-324 (Year: 2000).*

(Continued)

*Primary Examiner* — Stefanie J Cohen
(74) *Attorney, Agent, or Firm* — Procopio, Cory, Hargreaves & Savitch LLP

(57) ABSTRACT

The present invention relates to the field of material and, in particular, provides a material comprising a mixture of brown algae, a cellulosic material and an adhesive; it also relates to the process for the elaboration thereof that comprises the main steps of mixing the brown algae, the cellulosic material and the adhesive, and drying the mixture of the brown algae, the cellulosic material and the adhesive. The material of the present invention, therefore, complies with the fact of being a material applicable to different needs, with adaptable characteristics as a function of the proportion of its prime materials and low-cost. Additionally, since it is possible to use initial materials of fast recovering, as in the case of cactus and algae, or recycling materials such as of paper, it is shaped as an ecologically friendly material.

23 Claims, 5 Drawing Sheets
(1 of 5 Drawing Sheet(s) Filed in Color)

| N° | Plate | Density (kg/m³) | Absorption (%) | Humidity (%) | Flexure Strength (MPa) | (mm) | Maximum Deformation | Diameter of the mark (mm) | Surface Water Absorption (ml/min) |
|---|---|---|---|---|---|---|---|---|---|
| 1 | | 1118 | 21.84 | 4.9 | 14.8 | | 14.252 | 0 | 0 |
| 2 | | 1107 | 21.83 | 4.98 | 17.2 | | 10.963 | 0 | 0 |

(56) References Cited

U.S. PATENT DOCUMENTS

| | | | | |
|---|---|---|---|---|
| 5,472,569 A | * | 12/1995 | Nicolucci | D21C 5/00 162/148 |
| 5,532,405 A | | 7/1996 | Lyford, IV | |
| 6,392,034 B1 | | 5/2002 | Trusovs | |
| 7,607,240 B2 | | 10/2009 | Pinkham, Jr. et al. | |
| 8,496,748 B2 | | 7/2013 | Zikeli et al. | |
| 2010/0150972 A1 | * | 6/2010 | West | B65D 35/14 424/401 |
| 2012/0187226 A1 | * | 7/2012 | Tarverdi | D21B 1/12 241/21 |
| 2013/0068692 A1 | | 3/2013 | Thomas et al. | |

FOREIGN PATENT DOCUMENTS

| | | | | |
|---|---|---|---|---|
| WO | WO-2012114045 | A1 * | 8/2012 | D21B 1/04 |
| WO | 2015005868 | A1 | 1/2015 | |

OTHER PUBLICATIONS

Young et al, The Mucilage of Opuntia Ficus Indica: A Natural, Sustainable, and Viable Water Treatment Technology for Use in Rural Mexico for Reducing Turbidity and Arsenic Contamination in Drinking (Year: 2006).*

WO-2012114045-A1—english translation (Year: 2012).*

Justin's Amazing World at Fenner Paper, Apr. 2015 (Year: 2015).*

International Search Report for related PCT application PCT/CL16/050029, dated Oct. 17, 2016.

Hernandez-Zaragoza, J. B. et al., "Mejoramiento de Morteros a Traves de Nopal", J. PACD—2008, pp. 126-132. (Discussed in the Specification).

Leon-Martinez, F. M. et al., "Study of nopal mucilage and marine brown algae extract as viscosit-enhancing admixtures for cement based materials", Construction and Building Materials 53 (2014) pp. 190-202.

* cited by examiner

| Plate N° | Sample N° | Humidity (%) | Absorption (%) | Density (kg/m³) |
|---|---|---|---|---|
| 1 | 1 | 4.62 | 22.36 | 1.119 |
| 1 | 2 | 5.1 | 20.69 | 1.127 |
| 1 | 3 | 4.97 | 22.47 | 1.108 |
| 2 | 4 | 5.27 | 20.22 | 1.105 |
| 2 | 5 | 5.34 | 22.73 | 1.108 |
| 2 | 6 | 4.32 | 22.53 | 1.108 |

| Plate N° | Water Absorption (ml/min) | | | |
|---|---|---|---|---|
| | Sample N°1 | Sample N°2 | Sample N°3 | Average |
| 1 | 0 | 0 | 0 | 0 |
| 1 | 0 | 0 | 0 | 0 |

| Sample N° | Thickness (mm) | Diameter of the mark (mm) | | |
|---|---|---|---|---|
| | | Impact 1 | Impact 2 | Sample Average |
| 1 | 10.6 | 0 | 0 | 0 |
| 2 | | 0 | 0 | 0 |
| 3 | | 0 | 0 | 0 |
| Average (mm) | | | | 0 |

Fig. 4

| Sample N° | Thickness (mm) | Diameter of the mark (mm) | | |
|---|---|---|---|---|
| | | Impact 1 | Impact 2 | Sample Average |
| 1 | 10.5 | 0 | 0 | 0 |
| 2 | | 0 | 0 | 0 |
| 3 | | 0 | 0 | 0 |
| Average (mm) | | | | 0 |

Fig. 5

| Plate N° | Sample N° | Thickness (mm) | Span (mm) | Maximum Load (N) | Flexural strength (MPa) |
|---|---|---|---|---|---|
| 1 | 1 | 10.6 | 280 | 1206 | 14.8 |
| 2 | 2 | 10.6 | 280 | 1405 | 17.2 |

Fig. 6

| N° | Plate | Density (kg/m$^3$) | Absorption (%) | Humidity (%) | Flexure Strength (MPa) | (mm) | Maximum Deformation | Diameter of the mark (mm) | Surface Water Absorption (ml/min) |
|---|---|---|---|---|---|---|---|---|---|
| 1 | | 1118 | 21.84 | 4.9 | 14.8 | | 14.252 | 0 | 0 |
| 2 | | 1107 | 21.83 | 4.98 | 17.2 | | 10.963 | 0 | 0 |

Fig. 10

MATERIAL COMPRISING A MIXTURE OF BROWN ALGAE, CELLULOSIC MATERIAL AND AN ADHESIVE, AND PRODUCTION METHOD THEREOF

CROSS REFERENCE TO RELATED APPLICATIONS

This application is a U.S. National Stage entry of PCT Application No. PCT/CL2016/050029, filed on Jun. 3, 2016, which claims priority to the corresponding Chilean Patent Application No.: CL1932-2015, filed on Jul. 7, 2015, the entire contents of which are hereby incorporated by reference.

TECHNICAL FIELD OF THE INVENTION

The present invention relates to the field of technologies for solid waste management and, more specifically, to reuse, recycling or recovery technologies and in particular provides a material with multiple applications comprising a mixture of brown algae, cellulosic material and an adhesive, as well as the process for the elaboration thereof.

BACKGROUND OF THE INVENTION

Within the field of materials, the development of ecological materials has become relevant. In this sense, emphasis is given to materials, whose parent materials are recycling material such as paper or cardboard, or that constitute a parent material of fast regeneration, as in the case of algae and cactuses.

In the case of building materials, the use of different adhesives as additive in cementitious mixtures has been examined. In this sense, the nopal mucilage has shown to be an additive that enhances the compressive strength of the mortars and acts as a retardant in the fabrication of the same (Journal of the Professional Association for Cactus Development, Vol 10, pp 126-131). The use of nopal mucilage and brown algae extract as additives has been studied in other kind of mixtures, particularly their influence on the viscosity of the obtained mixtures (Construction and Building materials 53 (2014), 190-202), wherein both additives, separately, are found adequate for their use in cementitious mixtures for building. However, in said studies, the use of both additives together is not studied and the studies require said additives to be used in cementitious mixtures. In the previous cases, the use of cement has the disadvantage that it involves a high cost and a strong environmental impact, which are associated to its extraction. Furthermore, the application of mortars is restricted to its use in fixed buildings. Accordingly, there is a search for materials having a low environmental impact and a broad application range. Particularly, the elements originating from recycling play the role of providing a low cost raw material and lowering the environmental impact of the final product.

The state of the art describes materials using alga as one of its components. For example, the patent document U.S. Pat. No. 5,472,569 describes paper made from a cellulose paste and alga powder, wherein alga plays only an ornamental role.

Documents U.S. Pat. Nos. 8,496,748 and 7,951,237 disclose a polymer made from cellulose and particles of marine plants, as well as the process for the manufacture thereof. In one of the embodiments the use of algae as marine plant is considered; however, the process for the manufacture thereof comprises the step of dissolving the cellulose in a solvent selected from the group consisting of DMAc, DMSO, DMF and LiCl, and then mixing the dissolved cellulose with marine plant powder. The solvents used in this process can pose a risk to human health, so this process increases costs due to the related safety measures.

Finally, the document US 2004/228,984 describes a panel comprising a mixture of clay and vegetal material, wherein one of the embodiments thereof involves the use of algae paste as an additive in this mixture. However, in this last case, the algae paste is obtained by boiling a mixture of water and algae for a long time, which involves a cost increase and a greater use of the energy due to this step of the process. Additionally, this method for obtaining said paste implies that the algae are not completely use, since the useful portion seems to be the soluble component of the algae, which is obtained by boiling it. Other methods for obtaining said paste that involve a lower use of the energy are not described in this document.

Consequently, there is a need of providing alternative materials having adequate structural features and at low production cost, which can be obtained from the recycling of solid waste, for its use in a broad range of applications and involving a low environmental impact in its elaboration.

SUMMARY OF THE INVENTION

The present invention provides a material characterized in that it comprises a mixture of brown algae, a cellulosic material and an adhesive.

In a preferred embodiment, the brown algae are in ground or pulverized form to make up the mixture and they correspond to the *Durvillaea* genus. In a further preferred embodiment, the brown algae correspond to the species *Durvillaea antarctica*.

In another preferred embodiment, the material is characterized in that the cellulosic material is paper. In a further preferred embodiment, the paper is hydrated previous to its use, thus forming a paste.

In another preferred embodiment, the material is characterized in that the adhesive is selected from the group formed by mucilages and gums. In a further preferred embodiment, the material is characterized in that the mucilage is mucilage obtained from a cactus. In an even further preferred embodiment, the material is characterized in that the cactus corresponds to the *Opuntia* genus. In an even further preferred embodiment, the material is characterized in that the cactus is *Opuntia ficus-indica*

In an additional preferred embodiment, the material is characterized in that the mixture is pressed or layered. In a further preferred embodiment, the material is characterized in that the pressed or layered mixture has a thickness between 2 mm and 3 mm.

In another preferred embodiment, the material is characterized in that the dry weight ratio of ground brown algae to cellulosic material is between 3:1 and 1:2. In a further preferred embodiment, the dry weight ratio of ground brown algae to cellulosic material is 2:1.

In a preferred embodiment, the material is characterized in that the dry weight content of adhesive in the mixture is between 0.05% and 4%.

The present invention further provides a process for elaborating a material comprising the steps of:
  mixing ground brown algae with a cellulosic material and an adhesive; and
  drying said mixture of the ground brown algae, the cellulosic material and the adhesive.

In a preferred embodiment, the process is characterized in that it additionally comprises the step of pressing the mixture of the ground brown algae, the cellulosic material and the adhesive. In a further preferred embodiment, the process is characterized in that the mixture is arranged in a layered form before the pressing step. In a further preferred embodiment, the process is characterized in that the thickness of the layer of material is between 2 mm and 3 mm.

In another preferred embodiment, the process is characterized in that the step of mixing the ground brown algae with the cellulosic material and the adhesive comprises the steps of:
  mixing the ground brown algae with the cellulosic material;
  drying said mixture of ground brown algae and cellulosic material;
  pulverizing or milling said dry mixture; and
  mixing the adhesive and the powder or milling obtained from the step of pulverizing or milling said dry mixture.

In a further preferred embodiment, the process is characterized in that the drying of the mixture of ground brown algae and cellulosic material is performed at a temperature from 35 to 45 degrees Celsius. In another further preferred embodiment, the process is characterized in that the step of mixing the adhesive and the powder or milling obtained from the step of pulverizing or milling said dry mixture comprises the steps of:
  mixing the powder or milling obtained with a second amount of ground brown algae; and
  mixing the mixture obtained from the previous step with the adhesive.

In a preferred embodiment, the process is characterized in that the brown algae belong to the *Durvillaea* genus. In a further preferred embodiment the process is characterized in that the brown algae belong to the species *Durvillaea antarctica*.

In another preferred embodiment, the process is characterized in that the cellulosic material is paper.

In another preferred embodiment, the process is characterized in that the adhesive is selected from the group formed by mucilages and gums. In a further preferred embodiment, the process is characterized in that the mucilage is a mucilage obtained from a cactus. In an even further preferred embodiment, the process is characterized in that the cactus belongs to the *Opuntia* genus. In an even further preferred embodiment, the process is characterized in that the cactus is *Opuntia ficus-indica*

In another preferred embodiment, the process is characterized in that the dry weight ratio of ground brown algae to cellulosic material is between 3:1 and 1:2. In a further preferred embodiment, the dry weight ratio of ground brown algae to cellulosic material is 2:1.

In a preferred embodiment, the process is characterized in that the dry weight content of adhesive in the mixture is between 0.05% and 4%.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 4 shows the results of impact strength of a sheet of the material that is the subject of the present invention.

FIG. 5 shows the results of impact strength of a second sheet of the material that is the subject of the present invention.

FIG. 6 shows the results of flexural strength of two sheets of the material that is the subject of the present invention.

FIG. 10 shows the physical and mechanical characteristics of two sheets of the material that is the subject of the present invention.

DETAILED DESCRIPTION OF THE INVENTION

Figures 1, 2, 3:
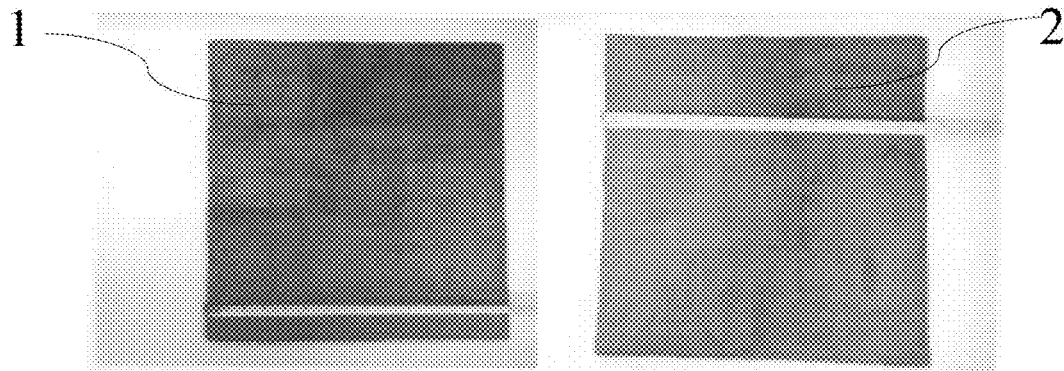
FIG. 1 shows two sheets of the material that is the subject of the present invention.
FIG. 2 shows the results of humidity, absorption and density of two sheets of the material that is the subject of the present invention.
FIG. 3 shows the results of surface absorption of two sheets of the material that is the subject of the present invention.

In a preferred embodiment of the invention, both the material that is the subject of the present invention as well as the process for the elaboration thereof are aimed at providing a layered material which can be used as a reinforcing or supporting material in different kind of industries, for example, as a separating panel in inner spaces.

However, it will be obvious for a person of ordinary skill in the art that the material that is the subject of the present invention can be used in other applications, without limiting the scope of the same. In this way, the material that is the subject of the present invention can be used, for example, for manufacturing containers or as a surface or structural material in furniture.

For elaborating the material of the present invention, in first place, brown algae are required, which are ground for this purpose. Said algae may be previously disinfected using, for example, chlorine, hydrogen peroxide, or other disinfecting agent. However, the disinfection of the algae does not limit the scope of the present invention.

Optionally, and without limiting the scope of the invention, the brown algae may also be dried before the grounding of the same. It is to be understood that brown algae are algae that belong to the Phaeophyceae class, as well as a combination of algae belonging to said class. A characteristic of said algae is that they are a good source of alginic acid, which is present in the cellular wall of the same.

A way for obtaining the ground brown algae is by pulverizing them. In this case, brown algae are pulverized until their two phases are powdered. It is to be understood that the two phases of brown algae are: an external cover, which is not soluble in water, and an internal component, which is soluble in water. Any technique capable of completely grounding the brown algae, i.e., keeping both phases, can be used in the previously described pulverization step, without limiting the scope of the present invention. For example, the document WO 2014/128,411 describes a method for obtaining a brown algae powder having a grain size ranging from 0.5 to 1.5 mm and a residual humidity lower than 45%. Nevertheless, the particle size or the humidity content of the ground brown algae do not limit the scope of the present invention.

In an alternative embodiment of the present invention, without limiting the scope of the same, it is possible to start with brown algae that are already ground or pulverized. This would be the case, for example, in which said powder is obtained from a supplier. Any brown algae powder that keeps both phases previously described is adequate to execute the present invention.

In second place, a cellulosic material is also required. It is to be understood that a cellulosic material is a material made, totally or partially, of cellulosic fiber including paper, in all its classes, paperboard or cardboard, as well as fabric or tissues containing cellulosic fibers of vegetal origin, for example, from wood, cotton, linen, jute, hemp and other plants. As an example, and without limiting the scope of the present invention, white paper and newspaper, as well as combination thereof, are considered as cellulosic material. Combinations of cellulose and some of its derivatives are also understood to correspond to this classification. The method, by which said cellulosic material is obtained, does not limit the scope of the present invention.

In a third place, an adhesive is required. Said adhesive can be organic or inorganic, from animal, vegetal or artificial origin. Within said adhesives, adhesives selected from the group formed by gums and mucilages, particularly and in a preferred way, mucilage from a cactus can be used. It is to be understood that a cactus is any plant belonging to the Cactaceae family, as well as combination of species belonging to said family. Within said family, a mucilage obtained from a species belonging to the *Opuntia* genus can be used, since it is possible to obtain a great amount of mucilage from the same, involving a low energy use in obtaining it. Nevertheless, neither the specific adhesive nor the way in which said adhesive is obtained limits the scope of the present invention. Said adhesive is complemented in its function by the binding property of the alginic acid from the brown algae in a synergic way, boosting the physical characteristics of the material that is the subject of the present invention.

Once the three previously described materials are obtained, the same are mixed until a uniform paste is obtained.

Due to the broad range of applications of material that is the subject of the present invention, the ratios in which those three materials are mixed will depend on the desired characteristics of the final product. In a general way, it was found that a greater amount of adhesive results in a more flexible material, whereas increasing the brown algae proportion generates a material having higher impact strength. The ratio of the ground brown algae to the cellulosic material can be varied in order to obtain a more or less compact material. A dry weight ratio of the ground brown algae to the cellulosic material from 3:1 to 1:2 can be used, without limiting the scope of the present invention. Additionally, and without limiting the scope of the invention, the dry weight content of the adhesive in the mixture can range from 0.05% to 4%. Different ways of preparing said mixing, as well as different proportions of the initial materials may be used, without limiting the scope of the present invention.

A way to prepare said mixing, without limiting the scope of the present invention, consists of mixing, in a first step, the ground brown algae with the cellulosic material, the latter preferably forming a paste as a result of a previous hydration. This mixture is then dried and, once it is dried, is milled or pulverized. Said drying may be done, without limiting the scope of the present invention, at a temperature from 35 to 45 degrees Celsius. In a preferred embodiment, it is possible to add a second amount of ground brown algae to said milled or pulverized mixture. In any of both cases, said mixture is mixed with the adhesive until a uniform mixture is obtained.

It is possible, without limiting the scope of the present invention, to press the previously obtained mixture in order to get a higher uniformity in the final material. In case this uniform paste is not pressed, the resulting material would have air bubbles inside it, which would provide the same with a higher thermal insulating capacity and a lower density, but, on the other hand, it would increase the fragility of the material and decrease the flexural strength of the same. In case said pressing is performed, the way in which the same is made does not limit the scope of the present invention.

After the mixture of the ground brown algae with the cellulosic material and the adhesive is obtained, the same is dried until obtaining the material that is the subject of the present invention. The method of drying said mixture does not limit the scope of the present invention. In a general way, the drying method should avoid the decomposition or denaturing of the alginic acid present in the brown algae powder. In an optional way, it is also possible, without limiting the scope of the present invention, to press the mixture once it is dried. As in the case in which the pressing is performed before the drying step, the way in which said pressing is done does not limit the scope of the present invention.

In case the pressing is performed, the same may be made arranging a layer of the mixture having a thickness from 2 mm to 3 mm and then performing the pressing. If the pressing is performed before the drying, it is possible to allow the pressed mixture to partially dry, press said layer, add a second layer having a thickness from 2 mm to 3 mm and press it a second time. It is possible to obtain layers of any thickness over 2 mm performing the previously described sequence in a successive way. The invention also considers the possibility of forming a sheet by the overlap of multiple layers. Said sheets are the sheets used in the tests of the material of the present invention.

Nevertheless, it is to be understood that arranging the material in a layered form represents a preferred embodiment, which does not limit the scope of the present invention. In the same way, in case the material is arranged in a layered form, the thickness of the same does not limit the scope of the present invention.

An example of embodiment of the present invention will be described hereinafter. It is to be understood that the scope of said example is to illustrate and to allow a better understanding of a way to perform the invention but should not, in any case, be considered to limit the scope of the same.

Example 1: Obtaining the Components of the Mixture

Brown algae of the species *Durvillaea antarctica*, commonly known as cochayuyo, are provided. Said cochayuyo can be collected in the shore, and, consequently, the same will be dry. This cochayuyo is ground using an electric mill until the two phases are powdered.

At the same time, paper, which can be used or new white paper, is provided. To execute this embodiment of the invention, the dry weight ratio between the paper and the cochayuyo powder is 2:1. This paper is soaked in water for a period of time enough to get it softened. In the case of the present example, the paper was soaked in water for a time of 10 hours. Once the paper is softened, a paste is made with the same. This paste corresponds to the cellulosic material which is a part of the mixture.

The cochayuyo powder is added to said paper paste, in such a way that the dry weight ratio of cochayuyo powder to paper was 1:1, and both components are mixed until obtaining a uniform mixture. The mixture so obtained is dried in air at a temperature between 35 to 45 degrees Celsius, in order to avoid the denaturing of the alginic acid present in the cochayuyo. The dry mixture is then pulverized using a grater and mixed with the remaining cochayuyo powder.

Finally, mucilage from a cactus is provided. In the case of the present example, said cactus is of the species *Opuntia ficus-indica*, commonly known as nopal. To obtain said mucilage, the paddles from the nopal are used, from which the wax and thorns are removed, obtaining the inner portion of said paddles. Said inner portion is cut into pieces and submerged in water. In the case of this example, the weight ratio of water to nopal paddles was 4:1 and the paddles from the nopal were submerged for twelve hours. After said period of time lapses, the solid parts of the nopal paddles are separated from the mucilaginous material which is part of the mixture.

The nopal mucilage obtained according to the previous process is mixed with the powder obtained from the pulverization of the dry mixture of cochayuyo powder and paper paste, obtaining a uniform paste that is a uniform mixture of ground brown algae—in this case cochayuyo, a cellulosic material—in this case paper paste, and an adhesive—in this case nopal mucilage. The dry weight content of the nopal mucilage in this final mixture ranges from 0.05% and 4%.

This particular way to prepare the mixture boosts the interaction between the alginic acid, present in the brown algae, and the adhesive, in this case the nopal mucilage, obtaining a colloid saturated material saturated of colloids, which give it a damping capacity before mechanical pressure to the material that is the subject of the present invention.

Example 2. Preparation of Sheets from the Obtained Material

Once the uniform mixture of the previous example is obtained, the same is arranged in form of layers having a thickness between 2 mm and 3 mm, partially dried in air and pressed. Once this first layer of material is dried, it is possible to add successive layers of material following the same procedure, that is, adding a 2 mm to 3 mm thick layer of the uniform paste, partially dry it, press it and wait for it to completely dry. In such a way, it is possible to obtain a layered material, of practically any thickness higher than 2 mm that forms a sheet, which is used to perform the tests that will be detailed hereunder. Due to the fact that all materials used in this example are of organic matter, the obtained sheets will be naturally biodegradable.

On the other hand, the process of sheets formation described in this example decreases the possibility of short term deterioration of the material, due to microorganism attacks, by avoiding the oxygen and humidity accumulation inside the sheets and providing minerals from the cochayuyo that contribute to increase the final pH of the material.

Additionally, the content of minerals of the final material allows it to be not flammable and to have a high flame resistance, which allows the material to slowly carbonize in the presence of fire.

Example 3. Determination of the Material Properties

Different tests to determine the physical (density, absorption and humidity) and mechanical properties of the material of the invention were performed for which two sheets (1 and 2), each having a surface of 40×40 $cm^2$, were used.

Relating to the mechanical properties, it was determined:
A curve of bending by tension with measure of the deformation
Compressive strength
Impact strength In order to determine the characteristics of the material that is the subject of the present invention, the procedures indicated in the following standards were used:

UNE-EN ISO 10545-3 (1997): Ceramical Tiles—Part 3: Determination of water absorption, apparent porosity, apparent relative density and bulk density.

NCh 146/2 Of.2000: Sheets or plates of plasterboard—Part 2: Tests methods.

The determination of the Surface Absorption was performed according to the document Measurement of Water Absorption Under Low Pressure Rilem Test Method N° 11.4.

The physical characteristics (humidity, absorption, density) can be observed in FIG. 2. It is possible to observe that the two sheets (1 and 2) have similar physical characteristics and have a relatively uniform density, slightly higher than the density of water.

Regarding the mechanical characteristics of the material, the surface water absorption of both sheets (1 and 2) can be observed in FIG. 3. It is observed that these sheets (1 and 2) do not show surface water absorption, which indicates that the sheets (1 and 2) obtained according to the present method have impermeability characteristics.

Relating to the impact strength, the results of said test can be observed in FIG. 4 for sheet (1) and in FIG. 5 for sheet (2). In both cases, the mark left by the ball used for this test is not observed, which suggests that the material has high impact strength.

Figure 7:
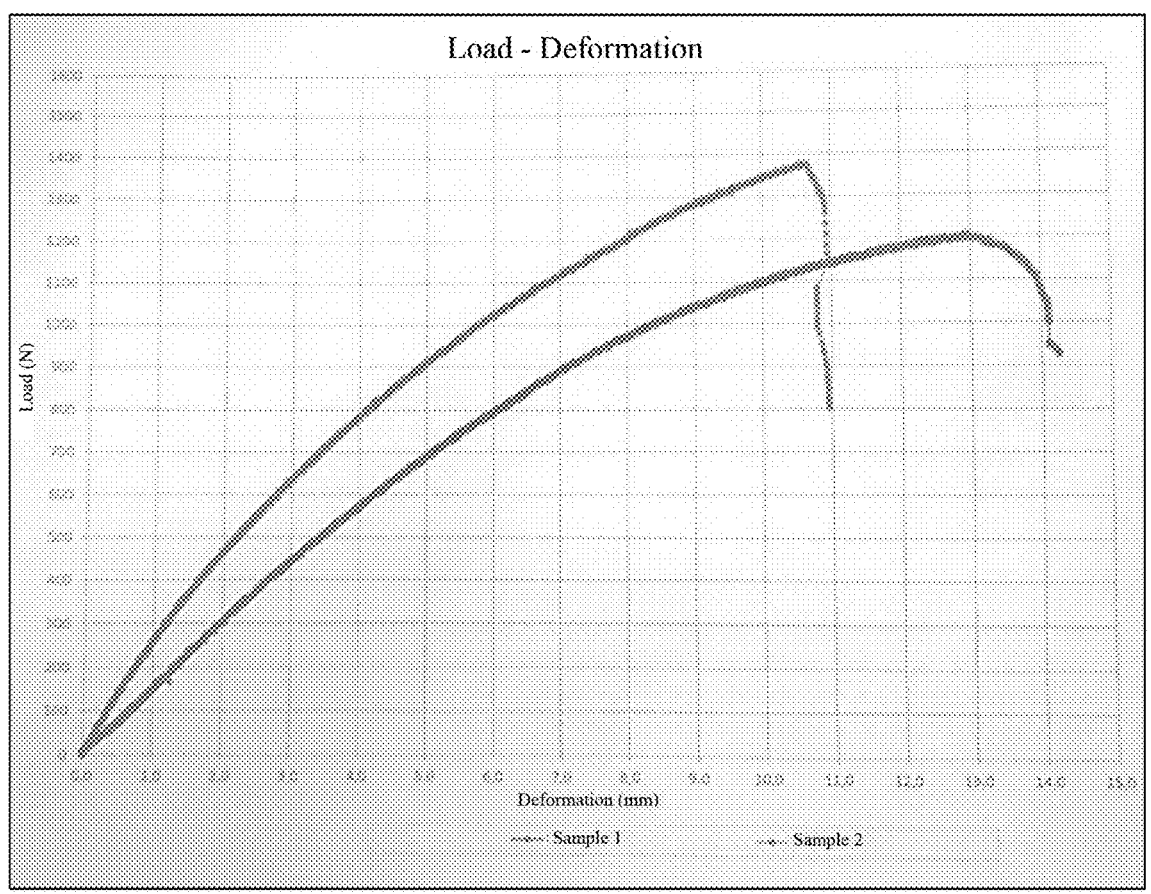
FIG. 7 shows the load curves against the deformation curves of two sheets of the material that is the subject of the present invention.
Figure 8:
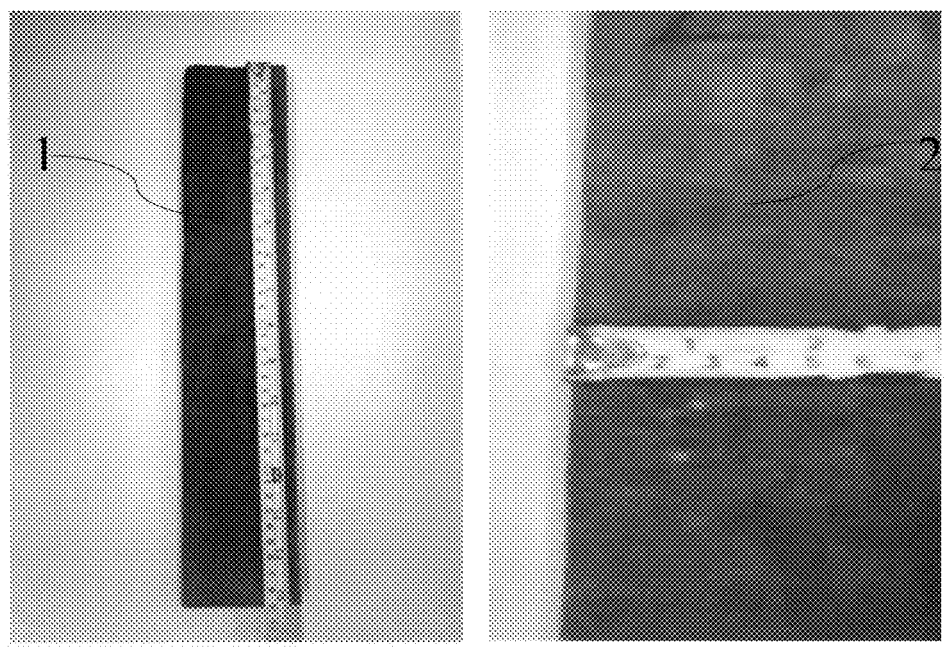
FIG. 8 shows two sheets of the material that is the subject of the present invention, which are used for the flexural strength test.

Regarding the flexural strength, the results for both sheets are observed in FIG. 6 and the plot of this test is shown in FIG. 7. Despite the fact of having similar dimensions, it is observed that both sheets (1 and 2) show different flexural strengths, but of comparable values between them. The sheets (1 and 2) used for this test are shown in FIG. 8.

Figure 9:
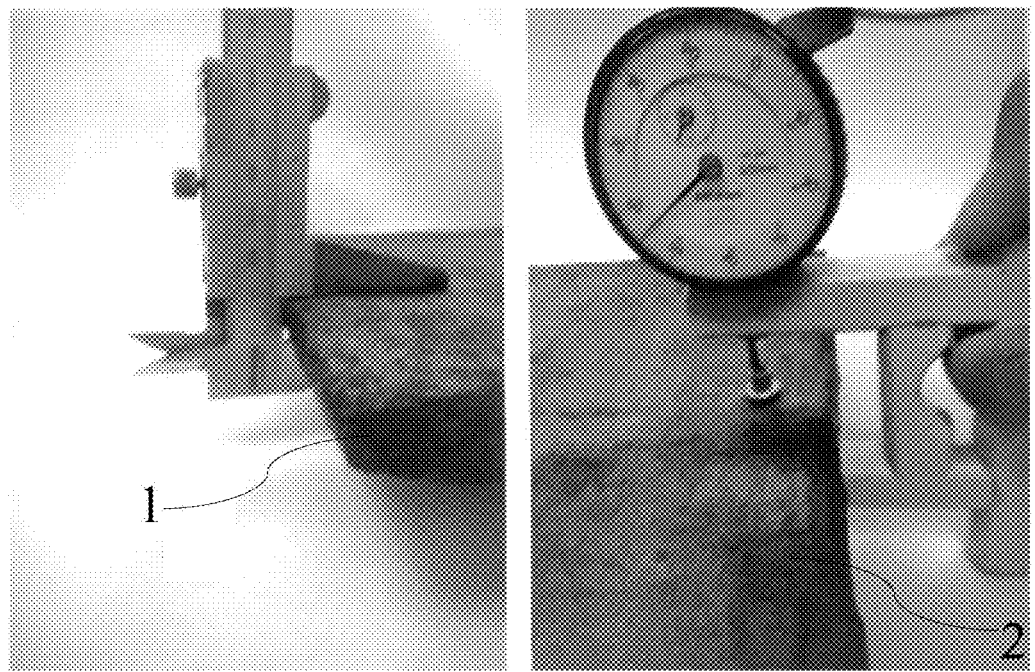
FIG. 9 shows the thickness measure of two sheets of the material that is the subject of the present invention.

Relating to the compressive strength, the current regulations for coverings similar to the material of the present invention do not consider the determination of the compressive strength, since it is not a relevant mechanical characteristic of those products. On the other hand, the geometrical condition of this kind of materials relating to its low thickness does not allow obtaining samples for this test. However, it must be noted that this is the case for the sheets (1 and 2) obtained in this example, but that the process that is the subject of the present invention, which was used in this example, allows obtaining sheets of practically any thickness over 2 mm. The determination of the thickness of the sheets (1 and 2) is observed in FIG. 9.

Finally, the physical and mechanical characteristics of both sheets (1 and 2) of the material that is the subject of the present invention are shown in FIG. 10.

It will be obvious for a person of ordinary skill in the art that some of the steps described in the present invention may be modified in order to optimize obtaining the material of the present invention. In that way, for example and without limiting the scope of the present invention, the nopal mucilage could be obtained by rehydrating powdered nopal mucilage. On the other hand, the procedure described in the present invention can be used both in a small scale as well as in an industrial level.

The material of the present invention, therefore, complies with the fact of being a material applicable to different needs, with adaptable characteristics as a function of the proportion of its prime materials, low-cost, since its elaboration does not involve expensive security measures associated to the process, as well as not necessarily requiring thermal treatments that increase the energetic cost of the same.

Additionally, since it is possible to use initial materials of fast recovering, as in the case of cactus and algae, or recycling materials such as paper, it is shaped as an ecologically friendly material.

The invention claimed is:

1. A flexible impact resistant material, comprising a mixture of:
 a) brown algae;
 b) a cellulosic material; and
 c) a mucilage obtained from a cactus;
 wherein said material is formed as a sheet comprising a plurality of layers of said mixture, and
 wherein said sheet has a thickness over 2 mm.

2. The material of claim 1, wherein the brown algae belong to the *Durvillaea* genus.

3. The material of claim 2, wherein the brown algae belonging to the *Durvillaea* genus belong to the species *Durvillaea antarctica*.

4. The material of claim 1, wherein the cellulosic material is paper.

5. The material of claim 1, wherein the cactus belongs to the *Opuntia* genus.

6. The material of claim 5, wherein the cactus is *Opuntia ficus-indica*.

7. The material of claim 1, wherein the mixture is pressed.

8. The material of claim 1, wherein the dry weight ratio between the brown algae to the cellulosic material is between 3:1 and 1:2.

9. The material of claim 8, wherein the dry weight ratio between the brown algae to the cellulosic material is 2:1.

10. The material of claim 1, wherein the dry weight content of mucilage in the mixture is between 0.05% and 4%.

11. A process for elaborating a flexible impact resistant material, comprising the steps of:
 a) mixing brown algae with a cellulosic material and a mucilage obtained from a cactus;
 b) forming a sheet comprising a plurality of layers of said mixture of the brown algae, the cellulosic material and the mucilage, wherein said sheet has a thickness over 2 mm; and
 c) drying said mixture of the brown algae, the cellulosic material and the mucilage.

12. The process of claim 11, additionally comprising the step of pressing said mixture of the brown algae, the cellulosic material and the mucilage.

13. The process of claim 11, wherein the step of mixing the brown algae with the cellulosic material and the mucilage comprises the steps of:
 a) mixing said brown algae and said cellulosic material;
 b) drying said mixture of the brown algae and the cellulosic material;
 c) milling or pulverizing the dry mixture obtained at step b); and
 d) mixing the mucilage and the powder or milling obtained at step c).

14. The process of claim 13, wherein the drying of the mixture of the brown algae and the cellulosic material is performed at a temperature between 35 and 45 degrees Celsius.

15. The process of claim 13, wherein the step of mixing the mucilage and the powder or milling obtained at step c) comprises the steps of:
 a) mixing the powder or milling obtained at step c) with a second amount of brown algae; and
 b) mixing said mixture obtained at step a) with the mucilage.

16. The process of claim 11, wherein the brown algae belong to the *Durvillaea* genus.

17. The process of claim 16, wherein the brown algae belong to the species *Durvillaea antarctica*.

18. The process of claim 11, wherein the cellulosic material is paper.

19. The process of claim 11, wherein the cactus belongs to the *Opuntia* genus.

20. The process of claim 19, wherein the cactus is *Opuntia ficus-indica*.

21. The process of claim 11, wherein the dry weight ratio of the brown algae to the cellulosic material is between 3:1 and 1:2.

22. The process of claim 21, wherein the dry weight ratio of the brown algae to the cellulosic material is 2:1.

23. The process of claim 11, wherein the dry weight content of mucilage in the mixture is between 0.05% and 4%.

* * * * *